(12) United States Patent
Sevenster et al.

(10) Patent No.: US 10,998,096 B2
(45) Date of Patent: May 4, 2021

(54) ANNOTATING MEDICAL IMAGES

(71) Applicant: KONINKLIJKE PHILIPS N.V., Eindhoven (NL)

(72) Inventors: Merlijn Sevenster, Haarlem (NL); Gabriel Ryan Mankovich, Boston, MA (US); Paul Joseph Chang, Chicago, IL (US)

(73) Assignees: KONINKLIJKE PHILIPS N.V., Eindhoven (NL); THE UNIVERSITY OF CHICAGO, Chicago, IL (US)

( * ) Notice: Subject to any disclaimer, the term of this patent is extended or adjusted under 35 U.S.C. 154(b) by 92 days.

(21) Appl. No.: 16/315,413

(22) PCT Filed: Jul. 17, 2017

(86) PCT No.: PCT/EP2017/067972
§ 371 (c)(1),
(2) Date: Jan. 4, 2019

(87) PCT Pub. No.: WO2018/015327
PCT Pub. Date: Jan. 25, 2018

(65) Prior Publication Data
US 2019/0259494 A1 Aug. 22, 2019

Related U.S. Application Data

(60) Provisional application No. 62/364,937, filed on Jul. 21, 2016.

(30) Foreign Application Priority Data

Oct. 19, 2016 (EP) .................................... 16194610

(51) Int. Cl.
*G06K 9/00* (2006.01)
*G16H 30/40* (2018.01)
(Continued)

(52) U.S. Cl.
CPC ............ *G16H 30/40* (2018.01); *G06F 19/321* (2013.01); *G16H 40/63* (2018.01); *G16H 50/20* (2018.01); *G06T 7/0012* (2013.01); *G16H 70/60* (2018.01)

(58) Field of Classification Search
CPC ............... G06T 7/0012; G06T 2200/24; G06T 2207/30004; G06T 2207/20076;
(Continued)

(56) References Cited

U.S. PATENT DOCUMENTS 7,546,293 B2 6/2009 Hong-Jiang et al.
8,423,538 B1 4/2013 Sadikov et al.
(Continued)

FOREIGN PATENT DOCUMENTS

WO WO-2015114485 A1 * 8/2015 ............. G06F 16/58

OTHER PUBLICATIONS

Ko, B.C. et al., "Automatic medical image annotation and keyword-based image retrieval using relevance feedback", Journal of Digital Imaging; The Journal of the Society for Computer Applications in Radiology, vol. 25, No. 4, Dec. 23, 2011, pp. 454-465.
(Continued)

*Primary Examiner* — Guillermo M Rivera-Martinez

(57) ABSTRACT

A system and method are provided for enabling a user to annotate a medical image. A collection of key-value pairs is provided, in which a key represents an image-observable quantity and a value represents the value of the image-observable quantity. A collection of structured finding objects is provided, wherein each structured finding object represents a set of key-value pairs, each set of key-value pairs representing a different annotation of the medical image. The user is enabled to select one or more of the collection of key-value pairs, thereby obtaining a user-selected structured finding object which represents a pre-
(Continued)

liminary annotation of the medical image by the user. At least one recommended structured finding object is selected by using the user-selected structured finding object as input to a probabilistic recommendation algorithm. Feedback is provided to the user on the basis of the recommended structured finding object. The annotation is well suited for, e.g., pointer-based selection via a graphical user interface, speech recognition, etc. Moreover, machine interpretability may be improved compared to conventional string-based annotation.

12 Claims, 5 Drawing Sheets

(51) Int. Cl.
    *G16H 50/20*    (2018.01)
    *G16H 40/63*    (2018.01)
    *G06F 19/00*    (2018.01)
    G16H 70/60    (2018.01)
    G06T 7/00    (2017.01)

(58) Field of Classification Search
CPC .......... G06T 2219/004; G06T 2210/41; G16H 50/20; G16H 30/20; G06K 9/6277; G06K 9/2054; G06K 9/6253; G06K 9/3233; G06K 9/6263; G06F 40/169
See application file for complete search history.

(56) References Cited

U.S. PATENT DOCUMENTS

| | | |
|---|---|---|
| 9,064,006 B2 | 6/2015 | Dilek et al. |
| 9,280,562 B1 | 3/2016 | Zhang et al. |
| 2006/0274928 A1* | 12/2006 | Collins .................. G16H 50/20 382/132 |
| 2010/0223258 A1 | 9/2010 | Ghahramani et al. |
| 2011/0110576 A1* | 5/2011 | Kreeger .................. G16H 50/20 382/132 |
| 2011/0170755 A1* | 7/2011 | Buelow .................. G06T 7/0012 382/128 |
| 2011/0182493 A1* | 7/2011 | Huber .................... G16H 30/20 382/132 |
| 2012/0020536 A1* | 1/2012 | Moehrle ............... G06F 19/321 382/128 |
| 2012/0159391 A1* | 6/2012 | Berry ..................... A61B 5/748 715/823 |
| 2012/0239653 A1 | 9/2012 | Platt et al. |
| 2013/0086067 A1 | 4/2013 | Khoussainova et al. |
| 2014/0219500 A1* | 8/2014 | Moehrle ............... G16H 30/20 382/103 |
| 2014/0379379 A1* | 12/2014 | Janevski ................ G16H 50/20 705/3 |
| 2015/0086133 A1* | 3/2015 | Grady ................ G06F 16/5866 382/278 |
| 2015/0347682 A1* | 12/2015 | Chen ..................... G16H 50/20 705/2 |
| 2015/0363485 A1 | 12/2015 | Bennett et al. |
| 2016/0034530 A1 | 2/2016 | Nguyen et al. |
| 2016/0098389 A1* | 4/2016 | Bruno .................. G06F 40/205 704/9 |
| 2016/0306791 A1* | 10/2016 | Allen .................. G06F 16/3329 |
| 2016/0335403 A1 | 11/2016 | Thusitha Dananjaya et al. |

OTHER PUBLICATIONS

Ching-Heng, L. et al., "Comparison of a semi-automatic annotation tool and a natural language processing application for the generation of clinical statement entries", Journal of the American Medical Informatics Association, vol, 22, No. 1, Jan. 1, 2015, pp. 132-142.

* cited by examiner

ANNOTATING MEDICAL IMAGES

CROSS-REFERENCE TO PRIOR APPLICATIONS

This application is the U.S. National Phase application under 35 U.S.C. § 371 of International Application No. PCT/EP2017/067972, filed on Jul. 17, 2017, which claims the benefit of U.S. Patent Application No. 62/364,937, filed Jul. 21, 2016 and European Patent Application No. 16194610.8, filed on Oct. 19, 2016. These applications are hereby incorporated by reference herein.

FIELD OF THE INVENTION

The invention relates to a system and a method for enabling a user to annotate annotating a medical image. The invention further relates to a workstation or imaging apparatus comprising the system. The invention further relates to a computer readable medium comprising instructions for causing a processor system to perform the method.

BACKGROUND OF THE INVENTION

Annotation of medical images is common practice in the medical field. For example, a radiologist may study a medical image and write down his/her observations and/or inferences from the observations, e.g., as part of a text report, as image labels, etc. In general, such annotations may be stored in the form of metadata of the medical image.

It is known to enter an annotation as a string in a text entry area of a user interface, e.g., of a radiology reporting tool. Moreover, it is known to, in general, provide string-based suggestions during text entry. For example, in the medical field, it is known to provide such string-based suggestions based on a controlled vocabulary, e.g., using a medical ontology such as SNOMED. A specific example are the string-based suggestions of the SNOMED CT browser, as may be accessed via browser.itsdotools.org.

Disadvantageously, the machine-interpretability of such string-based annotations are poor. In addition, known string-based suggestion techniques are typically limited to keyboard entry, and not easily applicable to other forms of user input.

WO 2015/114485 A1 describes a system and method which automatically determines a list of recommended annotations based on clinical context information. A user may select a desired annotation as one or a combination of such recommended annotations.

SUMMARY OF THE INVENTION

It would be advantageous to obtain a system and method for annotating medical images which addresses one or more problems of string-based annotations.

A first aspect of the invention provides a system for enabling a user to annotate a medical image, the system comprising:

a database interface configured to access a database comprising:

i) key-value data representing a collection of key-value pairs, wherein a key of a respective key-value pair represents an image-observable quantity and a value of the respective key-value pair represents the value of the image-observable quantity;

ii) object data representing a collection of structured finding objects, wherein each structured finding object represents a set of key-value pairs, each set of key-value pair representing a different annotation of the medical image;

a user interface subsystem configured to enable the user to select one or more of the collection of key-value pairs, thereby obtaining a user-selected structured finding object which represents a preliminary annotation of the medical image by the user;

a processor configured to select, from the collection of structured finding objects, at least one recommended structured finding object by using the user-selected structured finding object as input to a probabilistic recommendation algorithm, wherein the probabilistic recommendation algorithm is represented by a set of instructions stored as data in a memory accessible to the processor;

wherein the user interface subsystem is configured to provide feedback to the user on the basis of the recommended structured finding object.

A further aspect of the invention provides a workstation or imaging apparatus comprising the system.

A further aspect of the invention provides a method for enabling a user to annotate a medical image, the method comprising:

accessing a database comprising:

i) key-value data representing a collection of key-value pairs, wherein a key of a respective key-value pair represents an image-observable quantity and a value of the respective key-value pair represents the value of the image-observable quantity;

ii) object data representing a collection of structured finding objects, wherein each structured finding object represents a set of key-value pairs, each set of key-value pair representing a different annotation of the medical image;

enabling the user to, using user interface subsystem, select one or more of the collection of key-value pairs, thereby obtaining a user-selected structured finding object which represents a preliminary annotation of the medical image by the user;

selecting, from the collection of structured finding objects, at least one recommended structured finding object by using the user-selected structured finding object as input to a probabilistic recommendation algorithm; and providing feedback to the user on the basis of the recommended structured finding object.

A further aspect of the invention provides a computer readable medium comprising transitory or non-transitory data representing instructions arranged to cause a processor system to perform the method.

The above measures enable the annotation of medical images using so-termed structured multi-variate finding objects, in short also simply referred to as structured finding objects or SFOs. A SFO may be defined as a set of key-value pairs, e.g., $\{(k_1, v_1), \ldots, (k_n, v_n)\}$, with a key $k_n$ representing a quantity which is observable from a medical image being annotated, and the value $v_n$ representing a value of the image-observable quantity as may be observed from the medical image being annotated. Such key-value pairs may be pre-defined, e.g., generated before annotation, and accessed in the form of key-value data on a database. Optionally, a key-value pair, or a value of a predefined key, may be defined by the user during annotation, e.g., in a setup mode or in an edit mode during annotation.

The user may select one or more of such key-value pairs using a user interface. Together, this set of key-value pairs selected by the user may represent the SFO, which in turn may represent an annotation of the medical image by the user. A specific example is the SFO {(speculation, yes), (location, lung), (lobular location, left lower), (appearance, nodule)}, with, e.g., 'speculation' being an image-observable quantity, and 'yes' representing the quantity as observed by the user in the medical image.

To aid the user in the selection of a SFO, a recommendation may be provided to the user. For that purpose, a probabilistic recommendation algorithm may be used which uses the currently selected structured finding object as input, i.e., in the form of the one or more key-value pairs selected by the user. The currently selected SFO may represent a partial input from the user, in that the user may have started but not have completed entering the SFO by selecting key-value pairs, or may even have been deemed to represent a complete input of the SFO by the user. As output of the probabilistic recommendation algorithm, at least one other SFO may be identified which represents a recommended or suggested structured finding object in that the SFO is deemed to have a high probability of being selected and may thus be provided as a recommendation or suggestion. The probabilistic recommendation algorithm may be represented by a set of instructions stored as data in a memory. Feedback on the recommended SFO may be then be provided to the user, e.g., by visualizing the recommended SFO or a difference with the user-selected SFO.

The above measures enable a user to annotate a medical image by selecting one or more key-value pairs to form a structured finding object representing an annotation of the medical images. During the annotation, feedback from a probabilistic recommendation algorithm is provided to the user, e.g., to provide 'auto-completion' type of functionality. Advantageously, unlike the string-based entry and suggestion of annotations, the claimed measures to not require keyboard input but are well suited for, e.g., pointer-based selection via a graphical user interface, speech recognition, etc. Moreover, the structured finding object provides improved machine interpretability by being constituted by key-value pairs selected from a collection of predefined key-value pairs, rather than user-entered strings which may have to be matched to a controlled vocabulary to provide similar machine interpretability.

Optionally, the set of instructions, when executed by the processor, cause the processor to:

access a graph data structure representing the collection of structured finding objects, wherein respective nodes of the graph data structure represent respective structured finding objects, wherein an edge between a pair of nodes represents a change from one to another structured finding object as represented by the pair of nodes;

assign a node cost parameter to respective nodes of the graph data structure as a function of at least:

i) a probability parameter representing a probability of the structured finding object of a respective node being selected for annotation, and ii) one or more edge cost parameters which are assigned to respective edges of the graph data structure on a path between the respective node and a user node, the user node representing the user-selected structured finding object in the graph structure; and select the recommended structured finding object from the collection of structured finding objects by selecting a node of the graph data structure on the basis of said assigned node cost parameter.

It has been found that a representation of the collection of structured finding objects in the form of a graph data structure is particularly advantageous for estimating which structured finding object represents the desired annotation of the user. Namely, by generating and structuring a graph such that nodes represent structured finding objects and edges between pairs of nodes represent a change between the respective structured finding objects, it is possible to assign a cost parameter to the nodes based on a probability of a node being selected for annotation, and a cost parameter which represents the reachability of the node from the currently selected structured finding object. The latter may be calculated by assigning a cost to the edges of the graph, which may include but is not limited to an interaction cost representing a cost of effecting the change represented by the edge using the user interface subsystem. A non-limiting example is that the 'reachability' cost parameter may be assigned to a node based on a sum of edge costs along the shortest path towards the user-selected structured finding object. Having assigned a cost to the nodes of the graph data structure, one or more recommended structured finding objects may be selected from the graph data structure, e.g., based on their cost being minimal or below a certain threshold.

It will be appreciated by those skilled in the art that embodiments, implementations, and/or optional aspects of the invention may be combined in any way deemed useful. Modifications and variations of the method and/or the computer readable media, which correspond to the described modifications and variations of the system, can be carried out by a person skilled in the art on the basis of the present description.

It will be appreciate that the system and method may be applied to multi-dimensional image data, e.g., two-dimensional (2D), three-dimensional (3D) or four-dimensional (4D) images, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

BRIEF DESCRIPTION OF THE DRAWINGS

These and other aspects of the invention will be apparent from and elucidated further with reference to the embodiments described by way of example in the following description and with reference to the accompanying drawings, in which.

It should be noted that the figures are purely diagrammatic and not drawn to scale. In the figures, elements which correspond to elements already described may have the same reference numerals.

LIST OF REFERENCE NUMBERS

Figure 1:
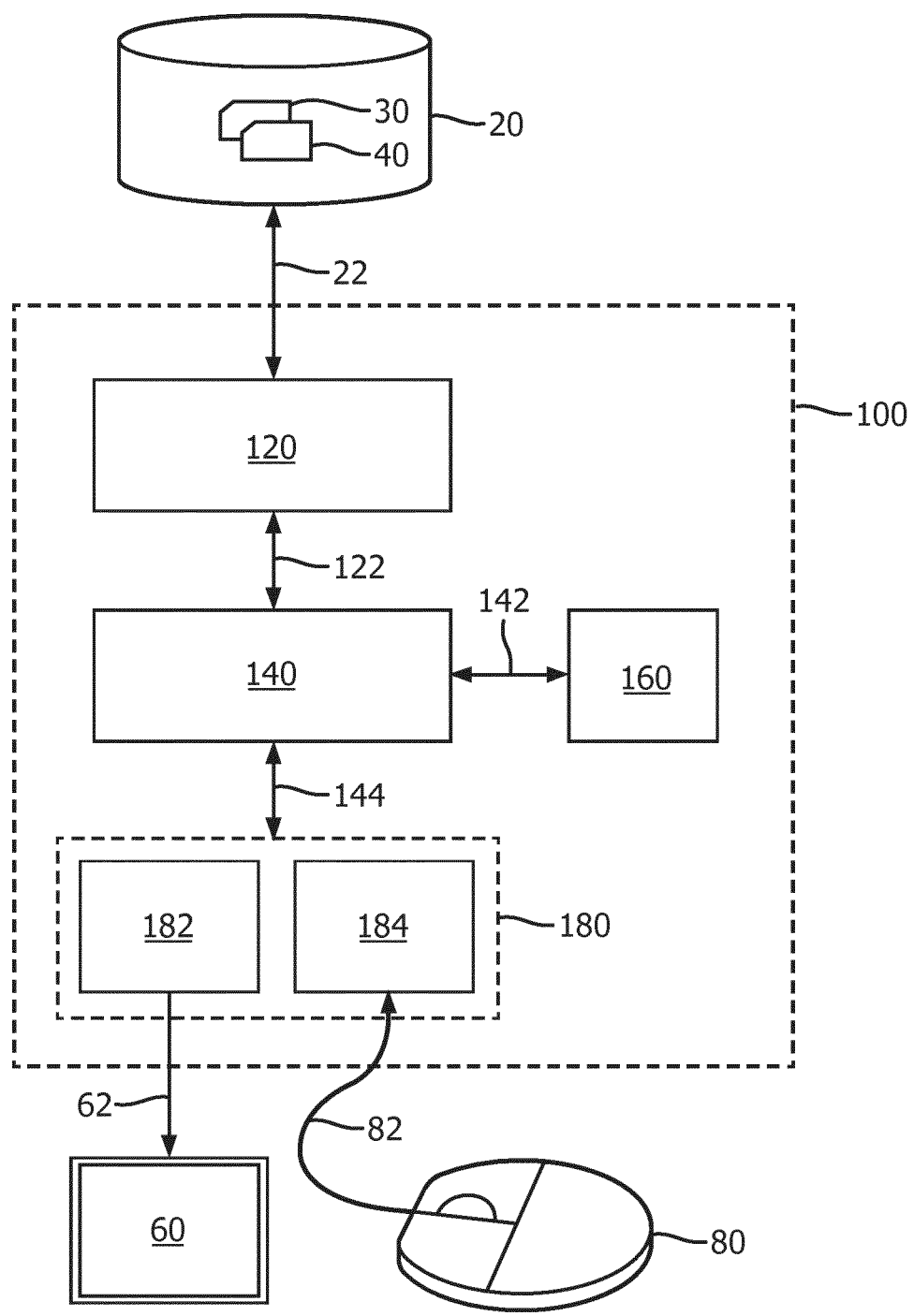
FIG. 1 shows a system for annotating medical images.

The following list of reference numbers is provided for facilitating the interpretation of the drawings and shall not be construed as limiting the claims.
020 database
022 database communication
030 key-value data
040 object data
060 display
062 display data
080 user input device
082 user input data
100 system for annotating medical images
120 database interface
122 internal data communication
140 processor
142, 144 internal data communication
160 memory
180 user interface subsystem
182 display processor
184 user input interface
200-206 visualization of structured finding object
210-218 visualization of key-value pairs
220, 222 visualization of alternative value
230 visualization of key-value pair type
250 addition symbol
260 deletion symbol
300 selection of deletion symbol
310 selection of alternative value
320 selection of addition symbol
330 selection of suggested key
400 graph data structure
410 node representing structured finding object
420 edge representing modification of key-value pair
430 edge representing addition/deletion of key-value pair
500 method for annotating medical images
510 accessing database
520 user input of structured finding object
530 selecting recommended structured finding object
540 providing feedback to user
600 computer readable medium
610 non-transitory data representing instructions

DETAILED DESCRIPTION OF EMBODIMENTS

FIG. 1 shows a system 100 for annotation of medical images. The system 100 is shown to comprise a database interface 120 configured to access, via respective data communication 022, a database 020 comprising key-value data 030 and object data 040. Here, the key-value data 030 may represent a collection of key-value pairs, wherein a key of a respective key-value pair represents an image-observable quantity and a value of the respective key-value pair represents the value of the image-observable quantity. Moreover, the object data 040 may represent a collection of structured finding objects, wherein each structured finding object represents a set of key-value pairs, and each set of key-value pair represents a different annotation of a medical image. It is noted that key-value pairs and structured finding objects will be further explained with reference to FIGS. 2-6.

FIG. 1 shows the database interface 120 accessing said data from a single database 020. However, the database interface 120 may also be configured to access the key-value data 030 and the object data 040 from different databases. For that purpose, the database interface 120 may be represented by, or comprise, two different sub-interfaces configured to access each respective database. In general, the data interface 120 may take various forms, such as a network interface to a local or wide area network, such as the Internet, a storage interface to an internal or external data storage, etc. Moreover, although shown in FIG. 1 to be an external database, the database 020 may also be an internal database.

The system 100 is further shown to comprise a processor 140 configured to internally communicate with the input interface 120 via data communication 122, a memory 160 accessible by the processor 140 via data communication 142, and a user interface subsystem 160 which comprises a display processor 162 and a user input interface 164 and is configured to internally communicate with the processor 140 via data communication 144.

The user interface subsystem 180 may be configured to, during operation of the system 100, enable a user to select one or more of the collection of key-value pairs, thereby obtaining a user-selected structured finding object which represents a preliminary annotation of the medical image by the user. For that purpose, the display processor 182 may be configured to generate display data 062 for a display 060 to establish a graphical user interface on the display, and the user input interface 184 may be configured to receive user input data 082 from a user device 080 operable by the user to enable the user to interact with the graphical user interface. Although shown in FIG. 1 to be an external display, the display 060 may also be an internal display. The graphical user interface may be represented by a set of interface instructions stored as data in a memory accessible to the display processor 182, being for example the memory 160 or another memory of the system 100. The user input device 080 may take various forms, including but not limited to a computer mouse, touch screen, keyboard, microphone, etc. FIG. 1 shows the user input device to be a computer mouse 080. In general, the user input interface 184 may be of a type which corresponds to the type of user input device 080, i.e., it may be a thereto corresponding user device interface.

The processor 140 may be configured to, during operation of the system 100, select, from the collection of structured finding objects, at least one recommended structured finding object by using the user-selected structured finding object as input to a probabilistic recommendation algorithm. The probabilistic recommendation algorithm may be represented by a set of instructions stored as data in the memory 160. Examples of probabilistic recommendation algorithms will be given in following sections of this description.

In general, the system of FIG. 1 may be embodied as—or in—a device or apparatus, such as a workstation or imaging apparatus. The device or apparatus may comprise one or more (micro)processors which execute appropriate software. The processor and display processor of the system may each be embodied by one or more of these (micro) processors, or by a same (micro)processor. Software implementing, e.g., the probabilistic recommendation algorithm, the graphical user interface and/or other functionality of the system, may have been downloaded and/or stored in a corresponding memory or memories, e.g., in volatile memory such as RAM or in non-volatile memory such as Flash. Alternatively, the processor and display processor of the system may be implemented in the device or apparatus in the form of programmable logic, e.g., as a Field-Programmable Gate Array (FPGA). The database interface and user input interface may be implemented by respective interfaces of the device or apparatus. In general, each unit of the system may be implemented in the form of a circuit. It is noted that the system may also be implemented in a distributed manner, e.g., involving different devices or apparatuses. For example, the distribution of the system may be in accordance with a client-server model.

Figure 2:
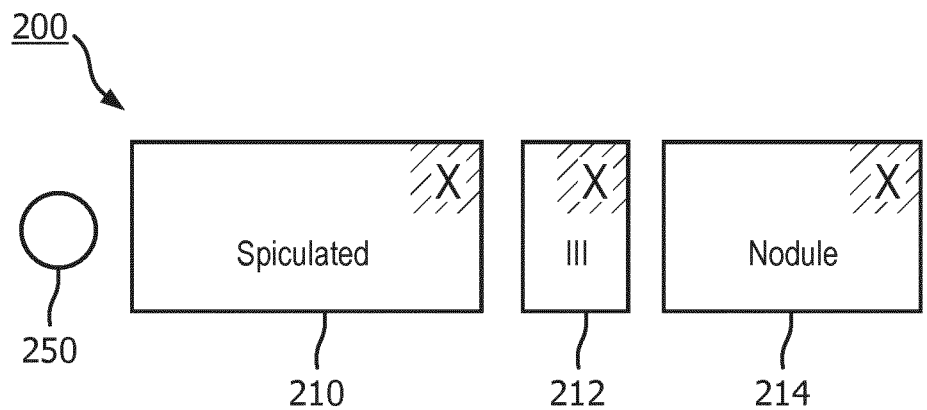
FIG. 2 shows a visualization of a structured finding object.

FIG. 2 shows a visualization of a structured finding object 200, henceforth also simply referred to as 'SFO'. In general, a SFO may comprise a set of key-value pairs $\{(k_1, v_1), \ldots, (k_n, v_n)\}$, with a key $k_n$ representing a quantity which is observable from a medical image being annotated, and the value $v_n$ representing a value of the image-observable quantity as may be observed from the medical image being annotated. In FIG. 2, the SFO 200 is represented in a simplified form, namely as values $\{v_1, \ldots, v_n\}$ of the key-value pairs, namely as 'spiculated' 210, 'lll' 212 and 'nodule' 214. The corresponding key-value pairs may be {(speculation, yes), (location, left lower lobe), (appearance, nodule)}. FIG. 2 further shows an addition symbol 250 which will be further described with reference to FIG. 5.

To appreciate the difference between string-based annotations and structured finding objects, consider the string 'spiculated left lower lobe nodule' which is typically abbreviated by 'spiculated lll nodule. This string may be decomposed in four semantic components, e.g., {(speculation, yes), (location, lung), (lobular location, left lower), (appearance, nodule)}, which may be represented by respective key-value pairs. It will be appreciated that the key-value pairs may be differently defined, e.g., in accordance with a data model of preference. As such, same or similar annotations may be differently represented. For example, the SFO of FIG. 2 is represented by {(speculation, yes), (location, left lower lobe), (appearance, nodule)}, or in short {spiculated, lll, nodule}, rather than the equivalent {{(speculation, yes), (location, lung), (lobular location, left lower), (appearance, nodule)}, which would be represent a same or similar annotation of a medical image. In general, values of key-value pairs may be numeric, e.g., a measurement value such as 3 cm or 21 mm, concepts from a medical lexicon or medical ontology (e.g., RadLex), free text, etc.

Manually entering a structured finding object may be cumbersome as it may involve a user specifying a key and a value of the key. If implemented in a straightforward manner, completion of simple SFOs may involve a high number of user interactions.

To facilitate entering SFOs, a graphical user interface may be provided by the user interface subsystem to facilitate the selection of SFOs. In addition, a probability-based recommendation system may be provided. The former will be described under "User interaction", whereas the latter will be described under "Recommendation algorithm".

User Interaction

The user interface subsystem of the system may, based on a set of interface instructions, generate a graphical user interface on-screen which enables a user to create and modify SFOs through a variety of simple user interactions. In the following, a specific graphical user interface is described, in which a SFO is visualized as an object in which each key-value pair is clearly distinguished as a box that may be deleted or whose content can be manipulated, e.g., as shown in FIG. 2. It will be appreciated that various other graphical user interfaces are within reach of the skilled person based on the present description.

Figure 3:
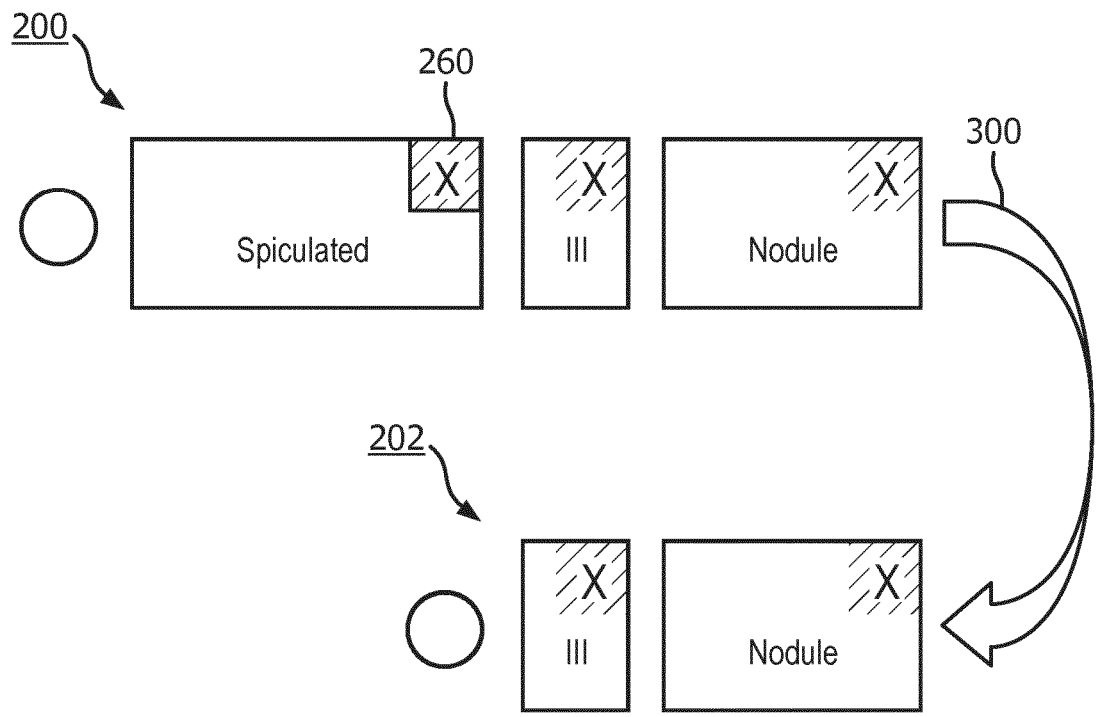
FIG. 3 illustrates the deletion of a key-value pair from the structured finding object using a graphical user interface.

FIG. 3 illustrates the deletion of a key-value pair from the structured finding object 200 using the graphical user interface. In order to delete a key-value pair, the user may select, e.g. using an onscreen pointer which is movable via a mouse, a graphical symbol which presents the deletion. For example, the graphical symbol may be a button 260 in the form of an 'X' which is positioned in the upper right corner of the box of each key-value pair. Accordingly, after selection of the button 260, which is shown in FIG. 3 by way of the curved arrow 300, the corresponding key-value pair may be deleted, resulting in a shortened SFO 202. The number of user interactions may be 1 selection, e.g., 1 mouse click.

It is noted that the relevance of the number of user interactions will be described with reference to the probabilistic recommendation algorithm.

Figure 4:
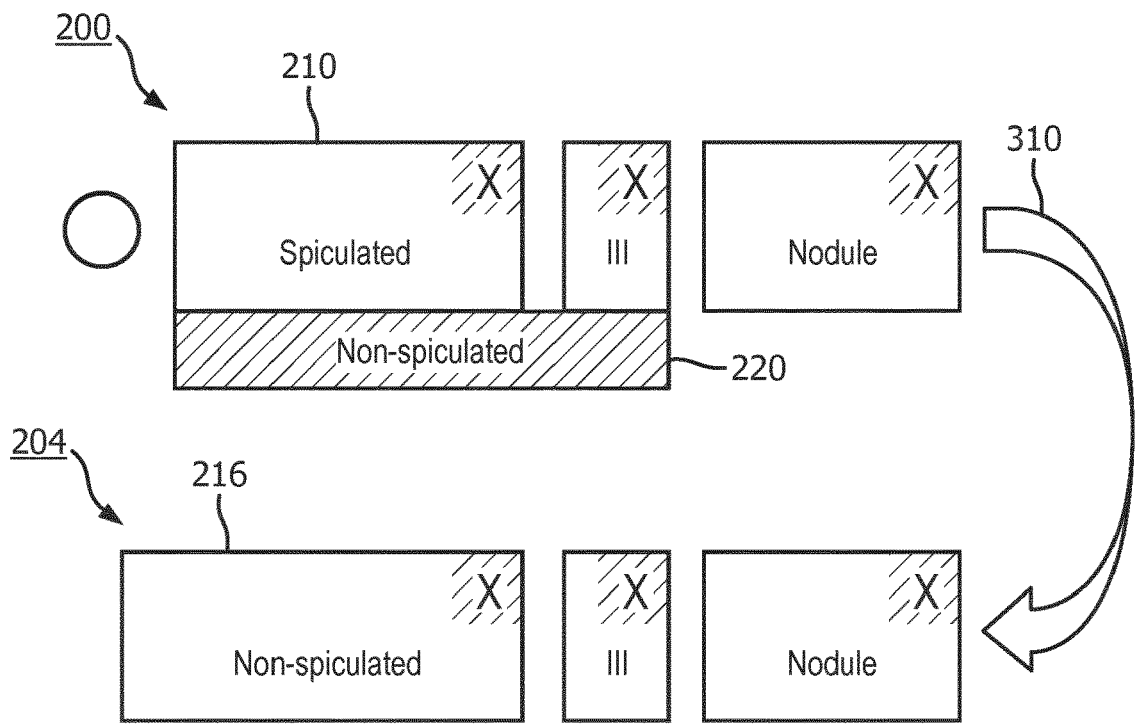
FIG. 4 illustrates the modification of a value of a key-value pair of the structured finding object using a graphical user interface.

FIG. 4 illustrates the modification of a value of a key-value pair of the structured finding object 200 using the graphical user interface. Here, in order to change a value, e.g., the value 'spiculated' 210, the user may hover with an onscreen pointer over the box representing the value and thus the associated key-value pair. The graphical user interface may then show alternative values, e.g., ranked by likelihood. Such likelihood may be determined by the probabilistic recommendation algorithm. In the example of FIG. 4, only one alternative value is shown, namely 'non-spiculated' 220. The user may then selected the alternative value 220 by clicking the corresponding box. Accordingly, after selection of the box, which is shown in FIG. 4 by way of the curved arrow 310, the corresponding key-value pair may be modified, resulting in a modified SFO 204 comprising the modified key-value pair {spiculated, no}, shown in FIG. 4 as 'Non-spiculated' 216. The number of user interactions may be 1 activation to activate the display of alternative values, e.g., a hovering of the pointer, and 1 selection to select the new value, e.g., a mouse click.

Figure 5:
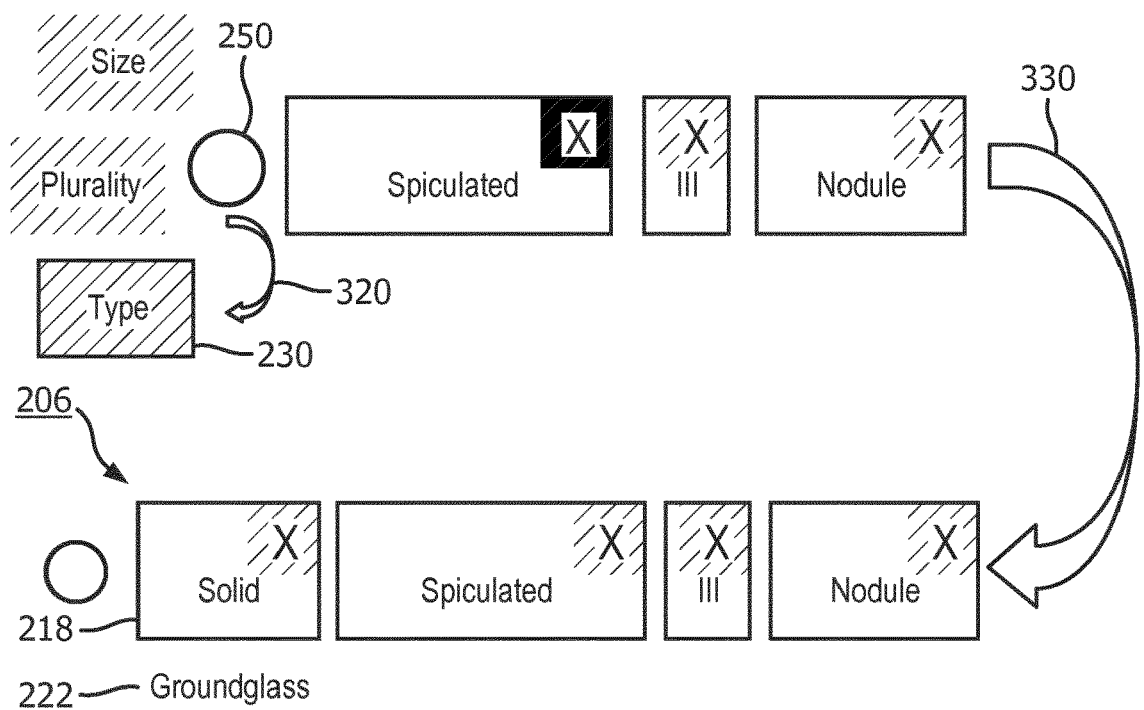
FIG. 5 illustrates the addition of a key-value pair to the structured finding object using a graphical user interface.

FIG. 5 illustrates the addition of a key-value pair to the structured finding object using the graphical user interface. Here, in order to add a key-value pair, the user may hover 320, e.g., with an onscreen pointer, over an addition symbol 250. The graphical user interface may display visual representation of a number of keys which are most likely to complement the SFO. Here, the keys may have been generated by the probabilistic recommendation algorithm, as will be described with reference to said algorithm. If the user selects 330 a preferred key, e.g., 'TYPE' 230, a new box may appear with the most likely value, 'solid', pre-filled, resulting in an SFO 206 comprising a new key-value pair {type, solid} 218. Optionally, the graphical user interface may also show alternative values for the key 'type', e.g., 'groundglass' 222, to enable easy selection by the user. The number of user interactions may be 1 activation to activate the display of the key-value pairs, e.g., a hovering of the pointer, and 1 selection to select the new key-value pair, e.g., a mouse click.

Recommendation Algorithm

In order to provide suggestions or similar feedback to the user on the basis of a user-selected SFO, a probabilistic recommendation algorithm may be used. Examples of such suggestions include, but are not limited, to those given with reference to FIGS. 2-5, e.g., alternative values of existing keys, new key-value pairs, etc. The following provides a description of a specific probabilistic recommendation algorithm. In general, any other suitable algorithms from the field of recommender systems may be used. It is noted that, although described predominately in terms of mathematical equations which are to be solved and pseudocode of a 'solver', the probabilistic recommendation algorithm is typically represented by a set of instructions stored as data in a memory accessible to the processor. It is within reach of the skilled person to implement the probabilistic recommendation algorithm in the form of such instructions on the basis of the present description.

Firstly, a three-place relation R may be defined such that R(L, M, c) indicates that one may obtain SFO M from SFO L by a set of user interactions having an interaction cost c. Examples of such sets of user interactions have been described with reference to FIGS. 2-5, and may pertain to one or more of the following actions, which are also simply referred to as 'changes' by effecting a change in a SFO: an addition of a key-value pair (henceforth also simply referred to as 'add a key'), a deletion of a key-value pair (henceforth also simply referred to as 'delete a key'), and a modification of a value of a key-value pair (henceforth also simply referred to as 'changing a value'), from one to another structured finding object.

In calculating the interaction cost of each actions, same weights be assigned each type of user interaction. Accordingly, the interaction cost of each action may be selected to be proportional to a number of user interactions needed to effect said action with the user interface subsystem. Alternatively, different weights be assigned to each type of user interaction. For example, a mouse click may be assigned a weight of 2, and hovering with a pointer a weight of 1. As such, the following actions may incur the following costs:
Delete a key: c=2
Change a value: c=3
Add a key: c=4

It will be appreciated that the interaction cost may also be differently calculated, and in general, may reflect the effort of effecting an action with the user interface.

Figure 6:
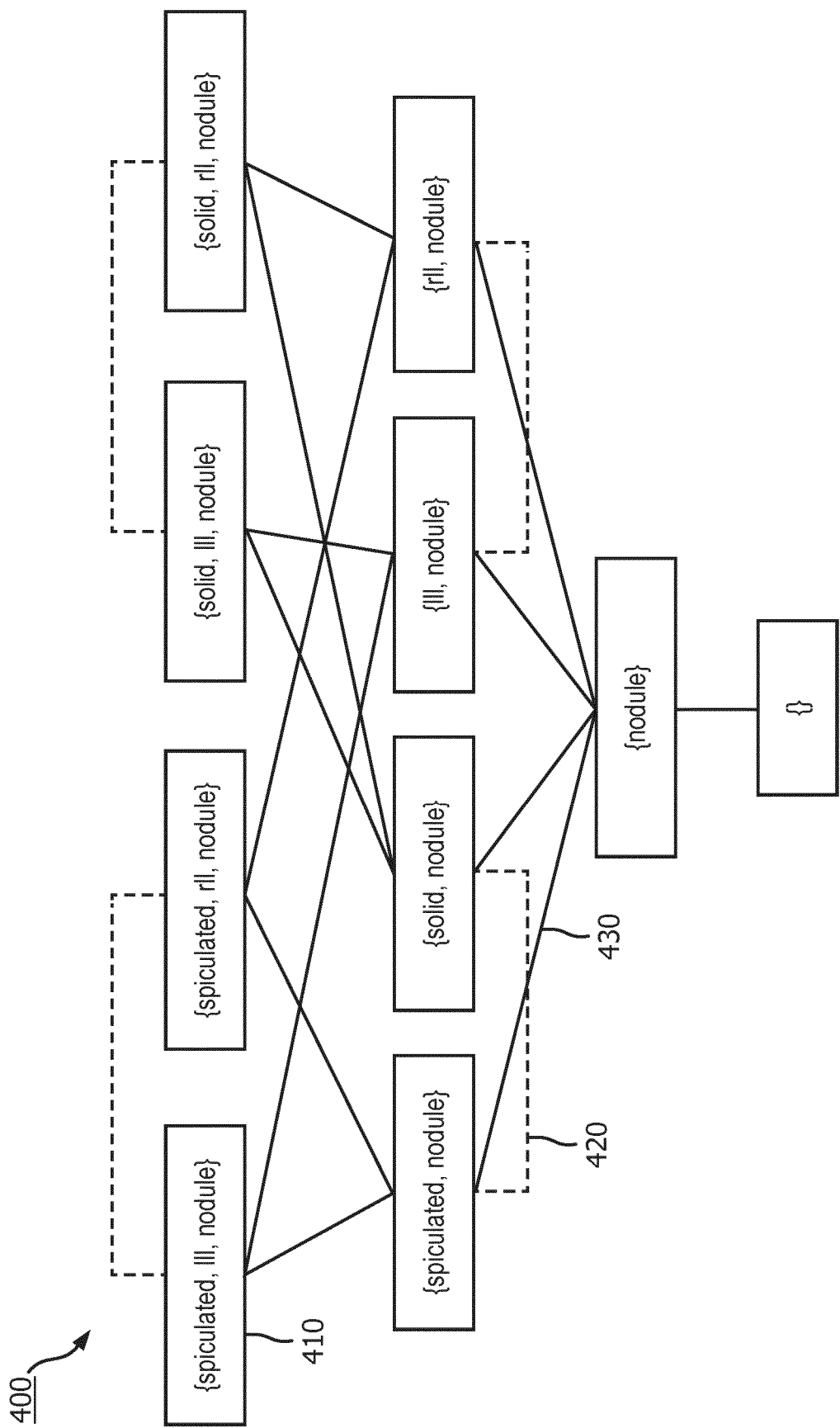
FIG. 6 shows a graph data structure representing a collection of structured finding objects, wherein respective nodes of the graph data structure represent respective structured finding objects, and wherein edges between pairs of nodes represents changes between the structured finding objects as represented by the respective pairs of nodes.

The probabilistic recommendation algorithm may make use of a lexicon, e.g., a collection of SFOs, which may be represented in a graph data structure. FIG. 6 shows an example of such a graph data structure 400. Here, respective nodes of the graph data structure 400 represent respective structured finding objects. For example, a node 410 may represent the SFO {spiculated, lll, nodule}. Moreover, edges between pairs of nodes may represent changes between the structured finding objects represented by the pairs of nodes. Here, different types of edges may represent different types of changes, which may include the changes effected by the above mentioned actions. For example, edges 420 represented by dotted lines in FIG. 6 may indicate that one SFO may be obtained from another by changing a value. Moreover, edges 430 represented by uninterrupted lines in FIG. 6 may indicate in an upward direction that a key-value pair is to be added, whereas the uninterrupted lines in downward direction may indicate that a key-value pair is to be deleted.

As such, for a given lexicon of SFOs and accessibility relation R defined for the lexicon, an interaction cost(L, M) may be defined as the minimal value d that may be defined as the sum of the interaction costs of any path between L and M in the relation R plus a constant d. In this manner, cost(L, L)=d. For example, the shortest path from the SFO {lll, nodule} to the SFO {spiculated, rll, nodule} in the graph data structure 400 may be:

{lll, nodule}»{rll, nodule}»{spiculated, rll, nodule} which may incur one 'value-change' interaction cost and one 'key-add' interaction cost, which may correspond to 7+d interaction units, if one assumes the previously mentioned interaction costs (e.g., delete a key: c=2, change a value: c=3, add a key: c=4). If, on the hand, c=1 is selected for all edges in R, then cost(L, M) may be identical to the length of the shortest path between L and M. For example, in the graph data structure 400 of FIG. 6, and assuming the cost c=1 for all edges, cost(L, M) between L={spiculated, lll, nodule} and M={solid, rll, nodule} may be 2. If c is equal for all edges in R, then cost(L, M) may be identical to c times the length of the shortest path between L and M.

The probabilistic recommendation algorithm may use the graph data structure 400 in the following manner in order to estimate a SFO that the user intents to enter. In recommending a SFO, the probabilistic recommendation algorithm may make use of the probability of a structured finding objects, being either an a-priori probability, a conditional probability or a combination of both. These probabilities may be determined as follows.

Let X be a set of SFOs $\{L_1, \ldots, L_m\}$, e.g., the SFOs of FIG. 6. Define $N_X(L)$ as the subset of SFOs M such that for all L' in X, cost(L, M)≤cost(L', M). Informally, $N_X(L)$ may contain all SFOs that are more easily obtained from L than from any other SFO L'.

Let P(L) be defined as an a-priori probability that the user intents to generate L, and P(L|Γ) as the conditional probability that the user intents to generate L given context parameter Γ which may be defined as a set of probability distributions, which may each describe a context. The probability functions in Γ may be obtained from contextual information, such as a probabilistic image segmentation algorithm and the observation that the SFO was triggered by a measurement. The use of contextual information will be further described. In general, a probability distribution F may be defined as a function that assigns to each element in its domain $\{x_1, \ldots, x_n\}$ a value in [0, 1] such that $$\sum_{x \in \{x_1, \ldots, x_n\}} F(x) = 1.$$

For example, if F is the output of a probabilistic image segmentation algorithm recognizing anatomical locations {lung, heart, liver, spine}, F might assign ⅔ to lung, ¼ to heart, ¼ to liver and 0 to spine. The notion of a probability distribution is very generic and may serve to model also less advanced, non-probabilistic context information. For example, for a given voxel, the output of a non-probabilistic image segmentation algorithm may simply be an anatomical location. In case, the output 'lung' may be modelled by a probability distribution that assigns 1 to 'lung' and 0 to all other anatomies. Similarly, binary variables may be modeled using probability distributions, e.g., by letting F(0)=1 if value 0 appears and F(1)=1 otherwise. As discussed further onwards, this may account for the event that an SFO is associated with a measurement, which is a binary variable.

Every time a recommended SFO is determined by the system using the probabilistic recommendation algorithm, the SFO may be stored by the system in combination with contextual information obtained by the system. Such contextual information may be obtained from various sources, including but not limited to metadata of the medical image, image analysis information obtained from an image analysis of the medical image, an image viewer application enabling the user to view the medical image, and logging information of the system. A specific example of image analysis information is the anatomical label of selected voxels, or a probability distribution over anatomical locations assigned to each voxel by the image analysis. Another specific example is that the system may 'listen' to the API of an image viewer application, e.g., as provided by a Picture Archiving and Communication System (PACS) viewing environment, to obtain contextual information in the form of detected user-initiated events. For example, whenever the user performs a measurement, this may represent contextual information: 'Measured=Yes'.

Accordingly, an annotation database may be generated which may comprises a row for each SFO L which has ever been entered and a column for every value $x_1$:

| SFO | $x_1$ | ... | $x_n$ |
|---|---|---|---|
| L | $F(x_1)$ | ... | $F(x_n)$ |

For example:

| | Anatomical location | | | | Measured? | |
| SFO | Lung | heart | spine | liver | Yes | No |
|---|---|---|---|---|---|---|
| Spiculated lll nodule | 0.8 | 0.1 | 0.1 | | 1 | 0 |
| Subcarinal lymph node | | 0.9 | 0.1 | | 0 | 1 |
| Subcarinal lymph node | | 0.95 | 0.05 | | 0 | 1 |
| Subcarinal lymph node | | 0.8 | 0.1 | 0.1 | 1 | 0 |
| Spiculated lll nodule | 0.9 | | 0.1 | | 1 | 0 |
| Spiculated lll nodule | 0.8 | 0.1 | 0.1 | | 1 | 0 |
| Spiculated lll nodule | 0.75 | 0.1 | 0.1 | 0.05 | 1 | 0 |
| Spiculated lll nodule | 0.8 | | 0.1 | 0.1 | 0 | 1 |

It will be appreciated that the probability values may not add up to one, but may readily be normalized by dividing each element by the sum. This annotation database, being an example of historical data and being in the following also referred to as 'contextual database', may be queried to obtain various probabilities, such as:

P(L): the a priori probability that L is the SFO a user intents to enter. This may be estimated as the number of times L appears in the database divided over the total number of SFO entered. In the above table, P('Spiculated lll nodule')=5/8 and P('Subcarinal lymph node')=3/8. As such, if no contextual information is given, it is almost twice as likely that 'Spiculated lll nodule' is the target SFO and not 'Subcarinal lymph node'.

P(L|lung): the conditional probability that L is the SFO a user intents to enter given that the pixel of interest is a lung pixel, or the body site is a lung, etc. This may be estimated as summing up all probabilities F(lung) for L and dividing it by the sum probability for all SFOs. In the above table, P('Spiculated lll nodule'|lung)=1 and P('Spiculated lll nodule'|liver)=(0.05+0.1)/(0.05+0.1+0.1)=0.15/0.25=0.6.

P(L|lung, measured=Yes): the conditional probability that L is the SFO a user intents to enter given that the pixel of interest is a lung pixel and triggered by a measurement. This may be estimated by summing up all probabilities F(lung)× G(measured=Yes) for L and dividing it by the sum F(lung)× G(measured=Yes) for all SFOs. In the above database, P(L|lung, measured=Yes)=1 and P('Spiculated lll nodule'|spine, measured=Yes)=(0.1+0.1+0.1+0.1)/(0.1+ 0.1+0.1+0.1)=0.8. As such, when current contextual information indicates that a lesion is measured which is located in the lung, this may increase the likelihood of the target SFO being 'Spiculated lll nodule' by 20%.

In general, suppose $\Gamma=\{F\}$. Let F' be the probability distribution of the same variable obtained from the contextual database. Then, P(L|F) may be defined as $$\sum_{x_i} F(x_i) P(L|x_i)$$

where $x_i$ ranges over the values on which the distribution F is defined, with the conditional probability P(L|xi) being obtained from the contextual database. In a similar way, P(L|{F,G}) may be defined as $$\sum_{x_i} \sum_{y_j} F(x_i) G(y_j) P(L|x_i)$$

where $x_i$ and $y_j$ range over the values on which the distributions F and G are defined, respectively. In a similar way, more complex context parameters $\Gamma=\{F, G, \ldots\}$ may be handled.

For an SFO L, a set of SFOs Y and context parameter $\Gamma$, define cost$\Gamma$(L, Y), also generally referred to as 'node cost parameter' of node L, as $$\sum_{M \in X} P(M|\Gamma) \text{cost}(L, M)$$

For a set of SFOs X, define cost$\Gamma$(X) as $$\sum_{L \in X} \text{cost}_\Gamma(L, N_X, (L))$$

Mathematically, the problem of finding an optimal set of SFOs in a given context $\Gamma$ may be considered as finding the set of SFOs X that minimizes cost$\Gamma$(X). Additional constraints may be imposed on this minimization problem, such as: X contains not more than 7 elements, no cost$\Gamma$(L, $N_X$(L)) exceeds a pre-determined threshold, etc.

It will be appreciated that this minimization problem may be compute intensive, if not theoretically intractable. To this end, it is appropriate to use approximation algorithms that achieve near-best solutions. The following pseudo-code may provide an approximation algorithm which aims to iteratively find the SFO with minimal cost. The approximation algorithm may be part of the probabilistic recommendation algorithm.

For an SFO, define $N_c$(L) as the set of SFOs M such that cost(L, M)<c. Thus, for example, $N_c$(L) may contain all SFOs that can be obtained from M with two mouse clicks. $\Gamma$ is a context vector; c is a numerical constant; X is the set of SFOs in the lexicon.

```
While (the set O contains < 7 SFOs or X is empty)
{
    L* = null;
    k = ∞;
    For each L in X do
    {
        Let X' be all elements in X that are not in Nc(L)
        l = cost(L, Nc(L)) + (ΣM in X' [P(M|Γ) × 100])
        If(l < k)
        {
            k = l
            L* = L
        }
    }
}
```

```
    Add L* to O
    Remove Nc(L) from X
}
```

This approximation algorithm iteratively seeks the SFO L that minimizes the cost for entering L itself, e.g., taking into account the interaction cost represented by edges in the graph data structure, and the cost of entering all SFOs that are accessible through L in c or fewer user interactions. The cost metric favors SFOs that are likely themselves, e.g., have a relatively high P(L) value, and that give access in the graph data structure to nodes of SFOs that are likely themselves, e.g., have relatively high probability values. The approximation algorithm gives a severe penalty, e.g., 100 user interaction units, for all SFOs that are not accessible from L in fewer than c user interaction units. This penalty will be lower if the likelihood of those SFOs not accessible from L are lower too. When an 'optimal' L* has been found, all SFOs that are accessible from L* in c or fewer user interactions are removed from the graph data structure and the search continues. The algorithm continues to find optimal SFOs until the graph is empty or a pre-determined number of SFOs has been found.

It will be appreciated that, by way of using SFOs for annotating medical images, the system is well suited for using speech recognition as user input. For example, the user interface subsystem may process user input from a microphone with any suitable known speech recognition algorithm to obtain a recognized string. The components of the recognized string may be compared against the values of known SFOs, e.g., as comprised in the database. For example, if the user articulates "annotate spiculated large nodule", the elements "spiculated", "large" and "nodule" may be compared against all values of key-value pairs in the database using exact or fuzzy string matching techniques. Matching elements may be presented to the user as an SFO. If, for example, "large" would have no match, the SFO {spiculated, nodule} may be presented. The user interface subsystem may be configured to make additional proposals using as additional context parameters the facts that the SFO must contain "spiculated" and "nodule". This may be modelled as discussed above.

Figure 7:
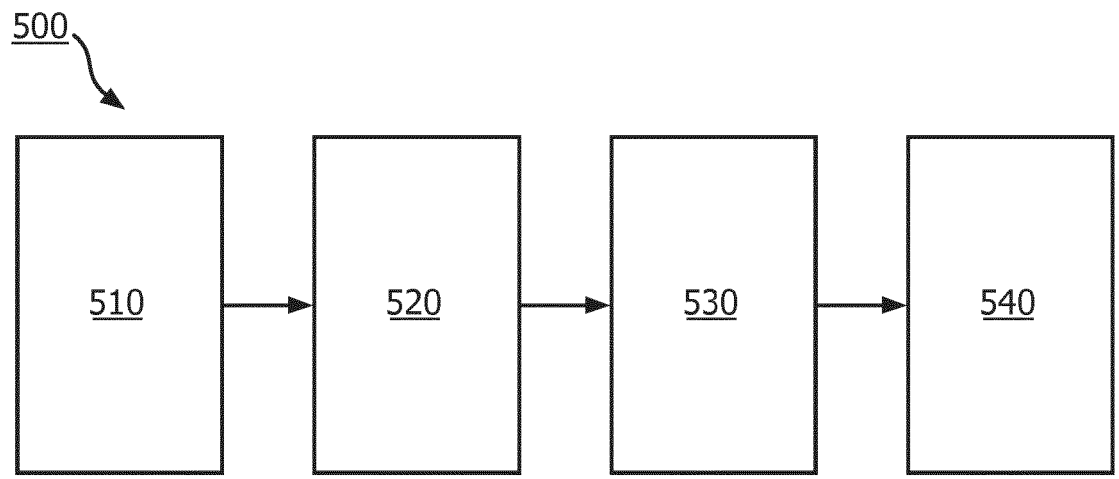
FIG. 7 shows a method for annotating medical images.

FIG. 7 shows a method 500 for annotating medical images, which may correspond to an operation of the system of FIG. 1. However, this is not a limitation, in that the method 500 may also be performed using a different system. The method 500 may comprise, in an operation titled "ACCESSING DATABASE", accessing 510 a database comprising key-value data and object data, e.g., as described with reference to FIG. 1. The method 500 may further comprise, in an operation titled "USER INPUT OF STRUCTURED FINDING OBJECT", enabling 520 a user to, using user interface subsystem, select one or more of the collection of key-value pairs, thereby obtaining a user-selected structured finding object which represents a preliminary annotation of the medical image by the user. The method 500 may further comprise, in an operation titled "SELECTING RECOMMENDED STRUCTURED FINDING OBJECT", selecting 530, from the collection of structured finding objects, at least one recommended structured finding object by using the user-selected structured finding object as input to a probabilistic recommendation algorithm, and in an operation titled "PROVIDING FEEDBACK TO USER", providing 540 feedback to the user on the basis of the recommended structured finding object.

Figure 8:
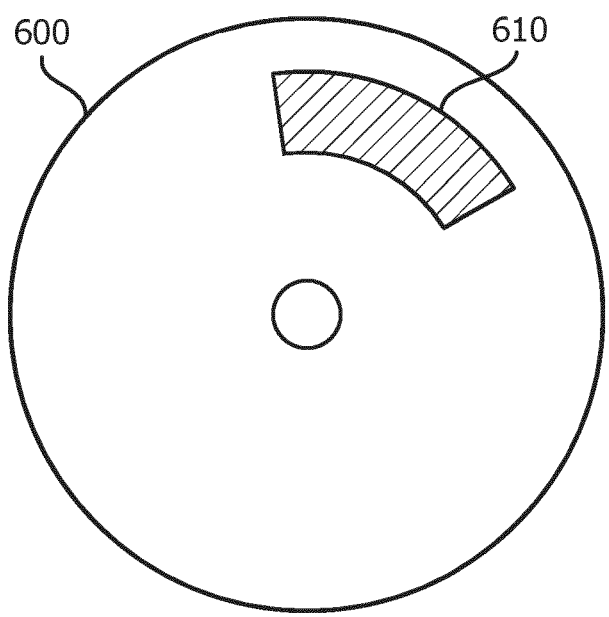
FIG. 8 shows a computer readable medium comprising instructions for causing a processor system to perform the method.

The method may be implemented on a computer as a computer implemented method, as dedicated hardware, or as a combination of both. As also illustrated in FIG. 8, instructions for the computer, e.g., executable code, may be stored on a computer readable medium 600, e.g., in the form of a series 610 of machine readable physical marks and/or as a series of elements having different electrical, e.g., magnetic, or optical properties or values. The executable code may be stored in a transitory or non-transitory manner. Examples of computer readable mediums include memory devices, optical storage devices, integrated circuits, servers, online software, etc. FIG. 8 shows an optical disc 600.

Examples, embodiments or optional features, whether indicated as non-limiting or not, are not to be understood as limiting the invention as claimed.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or stages other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for enabling a user to annotate a medical image, comprising:
   a database interface configured to access a database comprising:
   i) key-value data representing a collection of key-value pairs, wherein a key of a respective key-value pair represents an image-observable quantity and a value of the respective key-value pair represents a value of the image-observable quantity;
   ii) object data representing a collection of structured finding objects, wherein each structured finding object represents a set of key-value pairs, each set of key-value pairs representing a different annotation of the medical image;
   a user interface subsystem configured to enable the user to select one or more of the collection of key-value pairs, thereby obtaining a user-selected structured finding object which represents a preliminary annotation of the medical image by the user;
   a processor configured to select, from the collection of structured finding objects, at least one recommended structured finding object by using the user-selected structured finding object as input to a probabilistic recommendation algorithm,
   wherein the probabilistic recommendation algorithm is represented by a set of instructions stored as data in a memory accessible to the processor, wherein the set of instructions, when executed by the processor, cause the processor to:
   access a graph data structure representing the collection of structured finding objects, wherein respective nodes of the graph data structure represent respective structured finding objects, wherein an edge between a pair of nodes represents a change from one to another structured finding object as represented by the pair of nodes, wherein the change is one of a predetermined set of changes between the structured finding objects of the pair of nodes connected by the edge, wherein an edge cost parameter is assigned to the respective edges of the graph data structure based on an interaction cost function which is indicative of an interaction cost of effecting respective ones of the predetermined set of changes using the user interface subsystem;
   assign a node cost parameter to respective nodes of the graph data structure as a function of at least:
   i) a probability parameter representing a probability of the structured finding object of a respective node being selected for annotation, and
   ii) the edge cost parameters which are assigned to respective edges of the graph data structure on a path between the respective node and a user node, the user node representing the user-selected structured finding object in the graph structure; and
   select the recommended structured finding object from the collection of structured finding objects by selecting a node of the graph data structure on a basis of said assigned node cost parameter;
   wherein the user interface subsystem is configured to provide feedback to the user on a basis of the recommended structured finding object.

2. The system according to claim 1, wherein the predetermined set of changes comprises: an addition of a key-value pair, a deletion of a key-value pair, and a modification of a value of a key-value pair, from one to another structured finding object.

3. The system according to claim 2, wherein the interaction cost function assigns the interaction cost to each one of the predetermined set of changes proportional to a number of user interactions needed to effect said change with the user interface subsystem.

4. The system according to claim 1, wherein the path is a shortest path in the graph data structure between the respective node and the user node.

5. The system according to any one of the above claims, wherein the probability of the structured finding object comprises an a-priori probability determined from a number of occurrences of the structured finding object in historical data relative to the number of occurrences of other structured finding objects in the historical data.

6. The system according to any one of the above claims, wherein the probability of the structured finding object comprises a conditional probability determined from historical data as a function of contextual information obtained by the system and past contextual information comprised in the historical data.

7. The system according to claim 5, wherein the contextual information is obtained from at least one of: metadata of the medical image, image analysis information obtained from an image analysis of the medical image, an image viewer application enabling the user to view the medical image, and logging information of the system.

8. The system according to claim 5, wherein the historical data lists or is indicative of past annotations of past medical images.

9. The system according to any one of the above claims, wherein the user interface subsystem comprises:
   a display processor configured to generate display data for a display to establish a graphical user interface on the display; and
   a user input interface configured to receive user input data from a user input device operable by the user to enable the user to interact with the graphical user interface;
   wherein the graphical user interface is represented by a set of interface instructions stored as data in a memory accessible to the display processor, and
   wherein the set of interface instructions, when executed by the display processor, cause the display processor to generate a visualization of the recommended structured finding object, or a visualization of a difference between the recommended structured finding object and the user-selected structured finding object.

10. The system according to claim 9, wherein the set of interface instructions, when executed by the display processor, cause the display processor to:
   if the recommended structured finding object differs from the user-selected structured finding object by a deletion of a key-value pair from the user-selected structured finding object, generate a visual element representing the deletion;

if the recommended structured finding object differs from the user-selected structured finding object by an addition of a key-value pair to the user-selected structured finding object, generate a visual element representing at least the value of said added key-value pair; and/or if the recommended structured finding object differs from the user-selected structured finding object by a modification of a value of a key-value pair of the user-selected structured finding object, generate a visual element representing said modified value.

11. The system according to claim 1, wherein the system is a workstation or imaging apparatus.

12. A non-transitory computer readable medium comprising instructions arranged to cause a processor system to perform a method for enabling a user to annotate a medical image, comprising:

accessing a database comprising:
  i) key-value data representing a collection of key-value pairs, wherein a key of a respective key-value pair represents an image-observable quantity and a value of the respective key-value pair represents a value of the image-observable quantity;
  ii) object data representing a collection of structured finding objects, wherein each structured finding object represents a set of key-value pairs, each set of key-value pairs representing a different annotation of the medical image;

enabling the user to, using user interface subsystem, select one or more of the collection of key-value pairs, thereby obtaining a user-selected structured finding object which represents a preliminary annotation of the medical image by the user;

selecting, from the collection of structured finding objects, at least one recommended structured finding object by using the user-selected structured finding object as input to a probabilistic recommendation algorithm, and as part of an execution of the probabilistic recommendation algorithm:

accessing a graph data structure representing the collection of structured finding objects, wherein respective nodes of the graph data structure represent respective structured finding objects, wherein an edge between a pair of nodes represents a change from one to another structured finding object as represented by the pair of nodes, wherein the change is one of a predetermined set of changes between the structured finding objects of the pair of nodes connected by the edge, wherein an edge cost parameter is assigned to the respective edges of the graph data structure based on an interaction cost function which is indicative of an interaction cost of effecting respective ones of the predetermined set of changes using the user interface subsystem;

assigning a node cost parameter to respective nodes of the graph data structure as a function of at least:
  i) a probability parameter representing a probability of the structured finding object of a respective node being selected for annotation, and
  ii) the edge cost parameters which are assigned to respective edges of the graph data structure on a path between the respective node and a user node, the user node representing the user-selected structured finding object in the graph structure; and selecting the recommended structured finding object from the collection of structured finding objects by selecting a node of the graph data structure on a basis of said assigned node cost parameter; and providing feedback to the user on a basis of the recommended structured finding object.

* * * * *